US006395313B1

(12) United States Patent
Hull

(10) Patent No.: US 6,395,313 B1
(45) Date of Patent: May 28, 2002

(54) TREATMENT OF ARTHRITIS AND OTHER SIMILAR CONDITIONS

(76) Inventor: Peter Hugh Hull, 19 Lawson Street Midge Point, Queensland 4799 (AU)

( * ) Notice: Subject to any disclaimer, the term of this patent is extended or adjusted under 35 U.S.C. 154(b) by 0 days.

(21) Appl. No.: 09/701,503

(22) PCT Filed: Jun. 1, 1999

(86) PCT No.: PCT/AU99/00426

§ 371 (c)(1),
(2), (4) Date: Feb. 5, 2001

(87) PCT Pub. No.: WO99/62528

PCT Pub. Date: Dec. 9, 1999

(30) Foreign Application Priority Data

Jun. 1, 1998 (AU) .................................. 3796

(51) Int. Cl.[7] .............................................. A61K 35/78
(52) U.S. Cl. ...................................... 424/769; 424/725
(58) Field of Search .................... 424/725, 776

(56) References Cited

PUBLICATIONS

Pelomo et al., "Canarium Nut and Oil Marketing in Solomon Islands", South Pacific Indigenous Nuts, 1996, Editors M.L. Stevens et al., p. 76–78).*

Maima, "Processing of Galip (*Canarium indicum*) in Papua New Guinea", South Pacific Indigenous Nuts, 1996, Editors M.L. Stevens et al.*

Holdsworth, David. Int.J. Crude Drug Res. (1984) 22 No. 3, pp. 111–119 "Phytomedicine of the Madang Province, Papua New Guinea Part 1, Karkar Island."

Martin J et al, J.Sci.Food Agric. 1993, vol. 61, (3), pp. 383–384. "Chemical characteristics of canarium solomese oil."

Catalog product of Lansonn Skin Care Therapy Antioxidant.

International Search Report (PCT/AU 99/00426).

PCT International Preliminary Examination Report (PCT/AU 99/00426).

* cited by examiner

*Primary Examiner*—Leon B. Lankford, Jr.
*Assistant Examiner*—Ruth A. Davis
(74) *Attorney, Agent, or Firm*—Barnes & Thornburg

(57) ABSTRACT

Methods for treatment of arthritis are provided, the methods including administering an effective amount of Ngali Nut Oil.

15 Claims, No Drawings

TREATMENT OF ARTHRITIS AND OTHER SIMILAR CONDITIONS

CROSS-REFERENCE TO RELATED APPLICATIONS

This application is a U.S. national application of International Application Ser. No. PCT/AU99/00426, filed Jun. 1, 1999, which claims priority to Australian Provisional Patent Application No. PP3796 filed Jun. 1, 1998.

FIELD OF THE INVENTION

The invention relates to a method for treatment of the manifestations of arthritis and other similar conditions.

BACKGROUND OF THE INVENTION

Whilst the following discussion concerns the treatment and relief of the manifestations of arthritis, it is to be understood that the same principles apply to the treatment of the manifestations of rheumatism, tendinitis, spondylitis and similar degenerative joint disease.

Rheumatism is a general term which refers to any pain or ache originating from the muscles, joints, bones or other parts of the musculoskeletal system. Many people have rheumatic pains which vary from day to day and sometimes with the weather. Often sufferers report that their manifestations are worse when the weather is damp and cold, although other sufferers report the opposite. The reasons for these fluctuations, and the precise source and mechanism of the pain is not known.

Arthritis is a more specific term that implies damage or inflammation in one or more joints. The condition is often manifested by pain, swelling, heat, redness and limitation of movement. The most common type of arthritis is osteoarthritis or 'wear and tear arthritis'. The condition results from the wearing down of cartilage. Since the cartilage cannot be properly replaced by the body, it may make new bone at the edge of the joint to compensate for the loss of cartilage. This in turn produces bony swellings which are painful because the new bone is stretching the sensitive lining of the pre-existing bone. This condition is common in the fingers.

The cause of osteoathritis is unknown but may include a combination of chemical, mechanical, hereditary, metabolic, or endocrine factors which may damage a joint.

Hereditary osteoarthritis is a hereditary predisposition to a condition in which fingers and thumbs begin to go out of shape. This in turn causes bony swellings around the joint and the onset of arthritis. The condition seems to predominately affect women and manifests during menopause.

A genetic predisposition to osteoathritis, in conjunction with damage to the joint directly or indirectly may result in the condition manifesting itself in larger joints such as the hip and knee. This condition is seen predominately in men. Some occupations such as farming, and the pursuit of contact sports, have certain inherent risks towards the development of hip and knee osteoarthritis. A fracture involving a joint, a severe ligamentous injury, or removal of the patella usually results in the later development of arthritis in the area of damage.

Not as common but far more debilitating, is the condition known as rheumatoid arthritis. This involves the inflammation of the joints and affects 1 in 10 people. The inflammation starts in the lining of the joint and results in the release of pain causing substances into the joint space. It is also an auto immune disease in which the body's immune system attacks itself. There are many theories on the cause of rheumatoid arthritis. Although, it is thought a combination of environmental factors (such as infection) and genetic factors may make individuals more prone to the disease.

Unfortunately, there is no known way of halting the process of arthritis either by drugs or other methods. Current treatments include:

1. Joint Protection and Exercise

If a joint is diagnosed as being damaged either with signs of ligament damage or early manifestations of arthritis, sufferers are advised to avoid activities that may accelerate the arthritic process and rest the joint concerned. Dietary and weight loss programs are also prescribed.

Some form of exercise can also prove beneficial. However, because of the pain associated with arthritic manifestations, sufferers are often unable to comply with exercise regimes.

2. Drug Treatments

Several types of drugs are currently used in the treatment of arthritis including:

Pain Killers/ Analgesics.

These type of drugs are well known and include Aspirin, Paracetamol, Codeine and Diflunisal. They are important in allowing patients with chronic pain to cope with life and in some instances, sleep. Unfortunately these drugs are incapable of taking away the pain completely. Furthermore, overuse or overdependance can cause other problems such as gastrointestinal upsets and hemorrhage, tinnitus, dizziness, and hypersensitivity reactions to the drugs.

Non Steroidal Anti-Inflammatory Drugs

These types of drugs are also well known and include Voltaren, Arthrotec, Naproxen and Ketoprofen. These drugs reduce the formation of the prostaglandins responsible for the pain and inflammation associated with arthritis. They can reduce pain, swelling, stiffness and improve mobility. Unfortunately, they do not remove the manifestations of arthritis completely, and do not seem to cure the condition or prevent damage to the joints in the long term. This class of drugs have similar side effects to the Analgesics.

Disease-Modifying Drugs

These drugs are prescribed generally to combat rheumatoid arthritis. They can reduce the level of inflammation in the joints and prevent damage to the joints. Drugs in this class include Gold (Myocrisin), Sulphasalazine and Chloroquine. These drugs are slow acting and in some instances can take several months before taking effect. Unfortunately, a full cure is rarely achieved, and the treatment may have to be stopped because of the often harsh side effects such as dermatitis, skin rashes, anaphylactic hypersensitivity reactions, anorexia, nausea and vomiting.

Corticosteroids

Corticosteroids or steroids are prescribed to suffers of rheumatoid arthritis in particular. They can be effective in reducing the level of inflammation or in treating particularly painful arthritic flair ups. There is a reluctance to use, steroids more widely because of the long term side effects, particularly the suppression of the patient's own immune response and the adverse effects to the body's metabolic activities.

Recently, developments in stronger drugs and techniques which counteract the negative effects of chemical messengers (interleukins) have given arthritis sufferers renewed hope. However these drugs are still very much in the experimental phase.

Due to the high incidence of arthritis in the community, the financial burden of arthritis on the health system is extremely high.

Unfortunately the current drug regimes used for treating arthritis are only partially effective and in some instances, the side effects of continual treatment can outweigh the benefits. Unfortunately, dietary and exercise regimes have only limited application and are difficult to manage because of poor patient compliance.

In light of the inherent problems of current drug regimes, natural remedies are beginning to gain favor amongst arthritis suffers as an alternative means of treating their often painful manifestations. Natural remedies may therefore play an important role in relieving the manifestations of arthritis and because of a lack of side effects may result in better patient compliance.

Current natural remedies include Sea Cucumber Extract, Shark Cartilage, Green Lipped Mussel, Evening Primrose Oil and Cod Liver Oil. However there is no conclusive evidence that these remedies make much difference. Evening Primrose Oil and Cod Liver Oil are the most popular of the natural remedies and the ones with the best rationale of beneficial activity. It is possible that these remedies may alter the balance of the chemicals in the pain pathway in a favorable manner.

Accordingly, an investigation was made into the possibility of other natural remedies which could treat the painful manifestations of arthritis without some of the unwanted side effects associated with current drug regimes.

OBJECT OF THE INVENTION

It is an object of the invention to provide a method for treatment of the manifestations of arthritis using a naturally available composition.

SUMMARY OF THE INVENTION

It has surprisingly been found that an extract of Ngali Nut Oil can be effective in treating the manifestations of arthritis.

According to one form of the invention there is provided a method for treatment of the manifestations of arthritis in a mammal, including a human, by administering an effective amount of Ngali Nut Oil.

Preferably the Ngali Nut Oil is administered alone, or in combination with at least one other therapeutic agents used for treatment of the manifestations of arthritis. This may include compatible drugs.

Preferably the Ngali Nut Oil is administered topically to the epithelial surface of an area effected by manifestations of arthritis. The Ngali Nut Oil can be reapplied depending on the severity of the manifestations of arthritis.

According to another preferred form of the invention, the Ngali Nut Oil can be administered orally. The Ngali Nut Oil can be further orally administered depending on the severity of the manifestations of arthritis.

According to another form of the invention, a Ngali Nut Oil composition for topical administration is provided comprising:

a) not in excess of about 50% of a stable cream base; and
b) not in excess of about 50% Ngali Nut Oil.

The Ngali Nut Oil is mixed with the stable cream to form an emulsion. The stable cream acts as a base to facilitate the absorption of the Ngali Nut Oil into an epithelial surface of an area effected by the manifestations of arthritis.

There are several stable cream bases which may be used, these are well known to those skilled in the art.

One example of a stable cream base is Sorbolene Cream.
Preferably the percentage of Ngali Nut Oil is approximately 5%.

Typically, the composition of the present invention can be made by conventional compounding procedures known in the pharmaceutical art to provide a topically administered ointment, cream or paste.

According to another preferred form of the invention, a Ngali Nut Oil composition for oral administration is provided for the treatment of the manifestations of arthritis comprising an effective amount of Ngali Nut Oil.

The present invention provides a composition and a physiologically acceptable carrier suitable for oral administration.

For example, by mixing the active substance with edible physiologically acceptable, non toxic, inert, solid or liquid carriers and/or expicients suitable for systemic administration and conventionally used in oral dosage forms.

EXAMPLE

The invention will now be further explained and illustrated by the following non-limiting example.

Ngali Nut Oil is the oil obtained from the nuts of several varieties of Ngali Nut Trees grown in the Solomon Islands, Vanuatu Papua New Guinea and the Philippines. The three most common varieties of Ngali Nut Trees are *Canarium Indicium, Canarium Solomonesis* and *Canarium Harveyi*. At this stage no work has been done in creating hybrids of the Canariu species.

It will be understood by those skilled in the art that the current invention is not restricted to the aforementioned varieties of Ngali Nut Tree and includes any hybrids thereof.

The average oil content of the Ngali Nut is 74%, of which 48% is saturated fat. The type of fatty acids found are similar to Palm Oil, but with higher levels of stearic and linoleic acids.

TABLE 1

Ngali Nut Oil Analysis.

| | C. Harveyi (%) | C. Indicum (%) | C. Salomonense (%) |
|---|---|---|---|
| TOTAL OIL CONTENT[1] | 73.6 | 74.9 | 73.6 |
| FREE FATTY ACID CONTENT | .1 | .2 | |
| FATTY ACID COMPOSITION | | | |
| Lauric (C12:1) | | .4 | |
| Myristic (C14:1) | .1 | .2 | |
| Palmitic (C16:1) | 36.6 | 34.3 | 34.9 |
| Palmitoleic (C16:1) | .7 | .4 | |
| Heptadecanoic (C17:1) | .1 | .2 | |
| Stearic (C18:1) | 10.7 | 13.4 | 12.6 |
| Oleic (C18:1) | 26.3 | 37.5 | 41.6 |
| Linoleic (C18:1) | 24.5 | 13.5 | 10.3 |
| Linolenic (C18:1) | .3 | .3 | .4 |
| Arachidic (C20:1) | .3 | .3 | .2 |
| Eicosenoic (C20:1) | .1 | .1 | |
| Behenic (C22:1) | .1 | | |
| Saturated | 47.9 | 48.5 | 47.7 |
| Monosaturated | 27.2 | 37.8 | 41.6 |
| Polyunsaturated | 24.8 | 13.7 | 10.7 |

The Ngali Nut Tree is harvested to remove the Ngali Fruit. To extract the nut, the skin from the Ngali Fruit is removed and the in-shell nuts dried. The nuts are then cracked open to extract the kernel which is then pressed to extract the Ngali Nut Oil.

1. Composition

The composition tested comprised 5% Ngali Nut Oil and 95% of the stable cream base Sorbolene Cream.

2. Subjects

Six subjects, four males and two females, were recruited for this experiment aged between 50 to 89 years. The subjects suffered from, and had been diagnosed with most common varieties of arthritis including osteoarthritis and rheumatoid arthritis and exhibited typical arthritic manifestations including pain and inflammation of the joints.

In some instances, the subjects were already taking other medication including Analgesics, Non Steroidal Anti Inflammatory Drugs, Disease Modifying Drugs and Corticosteroids. The subjects maintained any pre-existing drug regimes.

3. Administration Regime

Initially, the subjects were instructed to apply a small amount of the Ngali Nut Oil composition twice daily, morning and night by rubbing it into the skin until all the composition was absorbed. When the arthritic pain began to dissipate the subjects were instructed to cut back the application and apply only when they felt a recurrence of pain. In most instances this resulted in a twice weekly or weekly application.

4. Assessment

The subjects were instructed to assess any change in the level of any arthritic manifestation. For the purposes of the experiment the arthritic manifestations were assessed by reference to the level of pain and immobility in the arthritic joint and the general well being of the subject. The last criteria encompassed both the physical and mental state of the subject.

5. Application of Ngali Nut Oil Composition

The Ngali Nut Oil composition was applied topically to the hands of the subject. The subject then proceeded to rub the composition until it was absorbed. Where possible, the hands were used as the test site because it is a part of the body which most readily shows signs of the manifestations of arthritis. Also, there is little surrounding tissue which the Ngali Nut Oil composition must penetrate in- order to reach the area exhibiting arthritic manifestations. Thus the Ngali Nut Oil composition could be absorbed quickly through the skin and reach the arthritic joints.

After initial application the subjects assessed the level of arthritic manifestations namely the level of pain, mobility and general well being on a weekly basis.

The Ngali Nut Oil composition was reapplied the same day, and applied twice daily there after, for a period of at least 2 weeks.

6. Results

In some instances, the subjects observed that the application of the Ngali Nut Oil composition resulted in a readily apparent reduction in the level of pain and immobility.

After two weeks of an initial twice daily application, subjects 1, 2, 3 and 4 showed a marked improvement in the reduction of arthritic manifestations.

At this point these subjects reduced the application of the Ngali Nut Oil composition to instances when the artitic manifestations began to re-emerge. Often this would result in weekly or twice weekly applications.

In the case of subjects 5 and 6, the marked improvement took longer than two weeks to show. They continued the application of Ngali Nut Oil composition twice daily until they also experienced a marked improvement in the incidence of arthritic manifestations. They then reduced the application of Ngali Nut Oil composition to instances when the arthritic manifestations began to re-emerge. This again resulted in weekly or twice weekly applications.

In all instances there was a decrease in the level of arthritic manifestations.

Subject 1 stopped the application of the Ngali Nut Oil composition after 4 weeks. He found that it took two months until the arthritic manifestations returned to their pre application level. This may indicate that the Ngali Nut Oil composition has some residual effect.

Subjects 3 and 4 showed signs of arthritic manifestations in both their hands, and in other parts of their body such as knees shoulder and back and ankles. After the Ngali Nut Oil composition had been applied twice daily for two weeks to their hands, these subjects reported that other areas effected by arthritic manifestations also began to show a reduction in these manifestations, specifically pain and immobility.

These subjects then applied a small amount of the Ngali Nut Oil composition directly to the area exhibiting arthritic manifestations twice daily, in the morning and in the evening. This led to a further decrease in the level of arthritic manifestations experienced by the subjects on the secondary areas of arthritic manifestations. This may indicate that the Ngali Nut Oil may have some systemic effect.

TABLE 2

Summary of Results

| Subject | Sex | Approx age | Type of pain | Existing medication | Location of Arthritic Manifestation | Period until some relief from Arthritic Manifestation | Residual effect | Systemic effect |
| --- | --- | --- | --- | --- | --- | --- | --- | --- |
| 1* | M | 62 | Osteoarthritis | NA | Fingers | 1 hour | Yes | Yes |
| 2 | M | 60 | Osteoarthritis | NA | Hand | 2 days | Yes | NA |
| 2 | M | 60 | Osteoarthritis Strain | NA | Lower back | 1 hour | Yes | NA |
| 3 | M | 60+ | Rheumatoid Arthritis | Predmisone Methotrexate Rodocol Indomethacin | All joints | 1 hour | Yes | Yes |
| 4 | F | 89 | Arthritis | Multi | Hand, shoulders, knees | 2 days | Yes | Yes |
| 5 | M | 60 | Osteoarthritis | NA | Wrist, Knee | 8 weeks 12 hours | Yes Yes | Yes |
| 6 | F | 50 | Non-arthritic | Steroid Injections | Wrist | 8 weeks | Yes | NA |

*Subject 1 stopped taking the Ngali Nut Composition, which lead to a return of the arthritic manifestations.

The above results indicate that Ngali Nut Oil can reduce the manifestations of arthritis.

The word 'comprising' and forms of the word 'comprising' as used in this description and in the claims does not limit the invention claimed to exclude any variants or additions.

Modifications and improvements to the invention will be readily apparent to those skilled in the art. Such modifications and improvements are intended to be within the scope of this invention.

What it claimed is:

1. A method for treatment of the manifestations of arthritis in a mammal by administering an effective amount of Ngali Nut Oil.

2. The method according to claim 1 wherein the Ngali Nut Oil is administered in combination with at least one other therapeutic agent used for treatment of the manifestations of arthritis.

3. The method according to claim 1 wherein the Ngali Nut Oil is administered topically to the epithelial surface of an area affected by the manifestations of arthritis.

4. The method according to claim 3 wherein the Ngali Nut Oil is reapplied depending on the severity of the manifestations of arthritis.

5. The method according to claim 1 wherein the Ngali Nut Oil is administered orally.

6. The method according to claim 5 wherein the Ngali Nut Oil is orally re-administered depending on the severity of the manifestations of arthritis.

7. The method according to claim 1 wherein the Ngali Nut Oil is administered topically in a composition comprising:
   a) a stable cream base; and
   b) not in excess of about 50% by weight of Ngali Nut Oil.

8. The method according to claim 7 wherein the stable cream base is Sorbolene Cream.

9. The method according to claim 7 wherein the amount of Ngali Nut Oil is by weight approximately 5%.

10. The method according to claim 1 wherein the Ngali Nut Oil is administered orally in a composition comprising:
    a) an effective amount of Ngali Nut Oil; and
    b) a physiologically acceptable carrier suitable for oral administration.

11. The method according to claim 1 wherein the mammal is a human.

12. A method for treatment of the pain and immobility of arthritis in a mammal comprising the step of administering an effective amount of Ngali Nut Oil to the mammal.

13. The method of claim 12 wherein the Ngali Nut Oil is administered topically to an epithelial surface of an area affected by pain and immobility of arthritis.

14. The method of claim 13 further comprising the step of reapplying the Ngali Nut Oil in a frequency sufficient to maintain reduction of the pain.

15. The method of claim 12 wherein the Ngali Nut Oil is administered orally.

* * * * *